(12) United States Patent
Fikatas

(10) Patent No.: US 10,172,610 B2
(45) Date of Patent: Jan. 8, 2019

(54) DEVICE AND METHOD FOR TYING A KNOT

(71) Applicant: Charité—Universitaetsmedizin Berlin, Berlin (DE)

(72) Inventor: Panagiotis Fikatas, Berlin (DE)

(73) Assignee: CHARITÉ—UNIVERSITAETSMEDIZIN BERLIN, Berlin (DE)

( * ) Notice: Subject to any disclaimer, the term of this patent is extended or adjusted under 35 U.S.C. 154(b) by 0 days.

(21) Appl. No.: 15/323,585

(22) PCT Filed: Jun. 4, 2015

(86) PCT No.: PCT/EP2015/062520
§ 371 (c)(1),
(2) Date: Jan. 3, 2017

(87) PCT Pub. No.: WO2016/005118
PCT Pub. Date: Jan. 14, 2016

(65) Prior Publication Data
US 2017/0143332 A1     May 25, 2017

(30) Foreign Application Priority Data

Jul. 7, 2014   (DE) .................. 10 2014 213 135
Mar. 19, 2015  (DE) .................. 10 2015 104 153

(51) Int. Cl.
A61B 17/04     (2006.01)

(52) U.S. Cl.
CPC .......... *A61B 17/0469* (2013.01); *A61B 17/04* (2013.01); *A61B 17/0483* (2013.01); *A61B 2017/0474* (2013.01); *A61B 2017/0477* (2013.01)

(58) Field of Classification Search
CPC ...... B65H 69/00; B65H 69/04; B65H 69/043; D04G 5/00; A61B 17/0469; A61B 2017/047; A61B 2017/0474; A61B 2017/0477; A61B 2017/0483; A61B 17/07; A61B 17/0483; B65B 13/24; B65B 13/26; A01F 15/145; A01D 59/04
See application file for complete search history.

(56) References Cited

U.S. PATENT DOCUMENTS 219,605 A * 9/1879 Travis
545,821 A   9/1895 Samuel
(Continued)

FOREIGN PATENT DOCUMENTS

WO    2004004577 A2    1/2004

OTHER PUBLICATIONS

International Search Report and Written Opinion dated Dec. 10, 2015 in PCT/EP2015/062520.

*Primary Examiner* — Ismael Izaguirre
(74) *Attorney, Agent, or Firm* — Fox Rothschild LLP

(57) ABSTRACT

The invention relates to a device (1) for tying a knot, said device comprising a thread (10) having a functional end (12) and a pull end (13). According to the invention, a main body (2) is provided and the thread (10) is laid around the outer surface (3) of said main body in the form of a prepared, still open knot (11), such that as a result of pulling on the pull end (13), the thread slides along the lateral surface (3) and forms a closed knot.

11 Claims, 12 Drawing Sheets

(56) References Cited

U.S. PATENT DOCUMENTS

Figure 1:
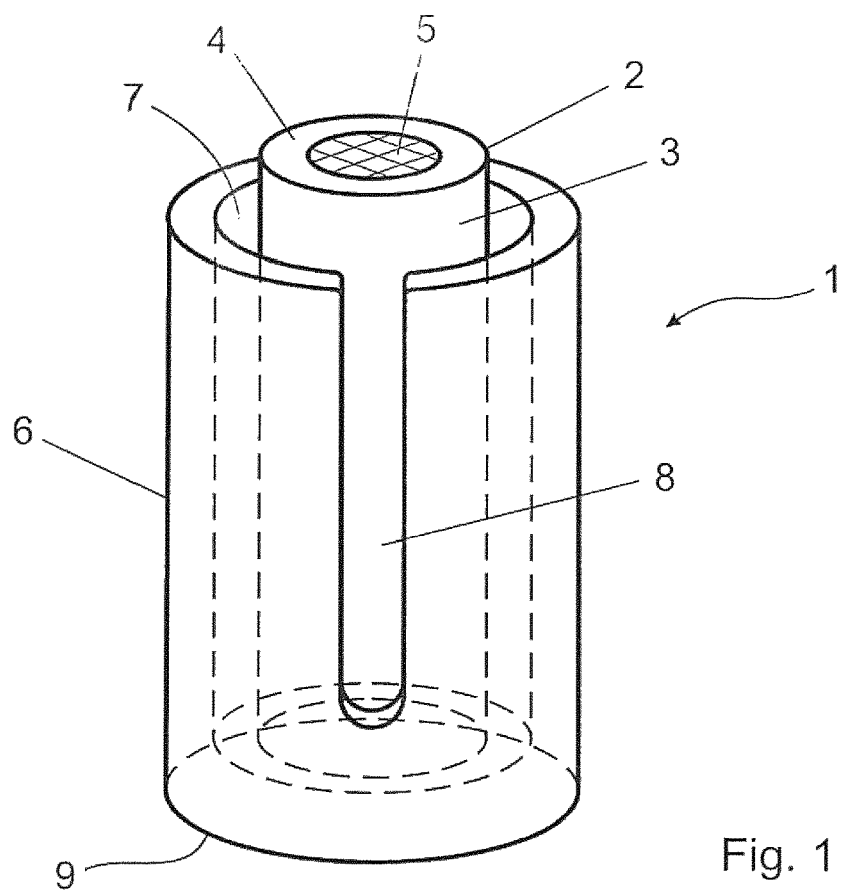

| | | | | |
|---|---|---|---|---|
| 1,474,265 | A | * | 11/1923 | Kenner .................. B65B 13/24 140/93 A |
| 3,476,423 | A | * | 11/1969 | Kentfield ............... B65H 69/00 289/17 |
| 4,403,797 | A | * | 9/1983 | Ragland, Jr. ........... A01K 91/04 289/17 |
| 5,217,470 | A | | 6/1993 | Weston |
| 5,643,293 | A | * | 7/1997 | Kogasaka .......... A61B 17/0469 112/169 |
| 5,716,368 | A | * | 2/1998 | de la Torre ........ A61B 17/0469 112/169 |
| 5,797,961 | A | * | 8/1998 | Smith .............. A61B 17/06066 112/222 |
| 5,893,592 | A | * | 4/1999 | Schulze ............ A61B 17/0469 289/1.2 |
| 6,540,267 | B1 | * | 4/2003 | Rohbock ................. D04G 5/00 289/1.2 |

* cited by examiner

DEVICE AND METHOD FOR TYING A KNOT

CROSS-REFERENCE TO RELATED APPLICATIONS

This application is a § 371 national stage entry of International Application No. PCT/EP2015/062520 filed Jun. 4, 2015, which claims priority to and the benefit of German Application No. 10 2014 213 135.9 filed Jul. 7, 2014, and German Application No. 10 2015 104 153.7 filed Mar. 19, 2015, all of which are hereby incorporated herein by reference in their entireties.

The invention relates to a device and a method for tying a knot.

Tying or closing knots in a thread, especially where space is limited, is difficult and time-consuming. This is especially the case if particular requirements concerning the strength or stability of the knot apply. Such usage can, by way of example, be found in sport, angling or packaging processes, or in medical technology.

The object of the invention, then, is to improve the tying of a knot.

This object is achieved with a device according to Claim 1. Advantageous embodiments can be found in the dependent claims.

The device according to the invention for tying a knot with a thread having a functional end and a pull end provides that a main body is provided, around the outer surface of which the thread in the form of a prepared, still open knot is laid, such that as a result of pulling on the pull end the thread slides along the outer surface and forms a closed knot.

The device according to the invention has the advantage that the knot is already prepared before use of the knot, so that during the actual creation or use of the knot this simply has to be tightened up. This saves time and makes knotting simpler, especially in applications that are difficult to access. The object to be knotted or joined with the thread can either be passed through a loop in the thread in the area of the functional end or the functional end can be brought into contact with, for example surround, the object and then the knot can be tightened.

A preferred embodiment of the invention provides that the functional end (12) can be attached to an attachment point of the main body (2). This simplifies handling because only one thread end is involved.

A preferred embodiment of the invention provides that the attachment point is arranged on an upper or lower top surface of the main body, on an inner surface of the main body or on the outer surface. The attachment point can be arranged on an outer surface of the main body, but also in the inside of the main body, for example in a slot or a recess. The attachment point can be provided as a function of the intended purpose or form of the main body. A number of attachment points can also be provided, wherein the most advantageous of these can be selected.

A further preferred embodiment of the invention provides that fastening means for connecting to an object and/or functional means for functionally connecting to an object are arranged on the thread before the functional end. The fastening means and/or functional means are preferably arranged in physical proximity to the functional end and can be arranged to be fixed or sliding, or detachable or nondetachable.

A preferred embodiment of the invention provides that the fastening means and/or the functional means comprise a needle, an anchor and/or a synthetic cord. The fastening means can, for example, comprise anchors, needles or hooks. The functional means can comprise functional elements such as synthetic cords or similar.

A preferred embodiment of the invention provides that flexible material is arranged at the attachment point and that a tip is arranged at the functional end, which is able to pierce the flexible material. In this way the functional end can be easily attached and any danger of injury from the tip, such as a needle, is also reduced.

A further preferred embodiment of the invention provides that the attachment point and the functional end are connectable by means of a snap-lock connection, a bayonet connection, a bonded connection or a lock connection, wherein the connection can be nondetachable or reclosable. Thus, the functional end can for example be joinable by clip or hook. These connections can be opened and/or closed either once or multiple times.

A further preferred embodiment of the invention provides that an enveloping body surrounding the main body and thread is provided, wherein the enveloping body comprises at least one opening arranged in the area of the lateral surface for the functional end and/or the pull end. The enveloping body, which is preferably slightly shorter in the lengthways or axial direction than the main body, protects the laid thread and simplifies handling.

It is particularly advantageous if the main body has a configuration that is cylindrical, conical, rectangular, prismatic or spoke-like with radial spurs. When the pull end is pulled, the thread then slides easily in the direction of the functional end or the main body can be optimally adapted to the thread, knot and/or intended purpose. The main body can be solid, provided with recesses, or hollow, like a pipe, for example.

The thread can comprise an adaptation knot turned towards the functional end and a safety knot turned towards the pull end. This allows a modular adaptation of the knot to the task in question. By means of the adaptation knot or adaptation knot area, which can also be termed a functional knot or functional knot area, the properties of the knot such as the strength, tightening behavior, size and so on are defined. The safety knot or safety knot area serves to secure the adaptation knot against unintentionally coming loose or unknotting.

It is preferably provided that the thread is laid at least twice around the main body in a first direction and at least once around the functional end in a second direction. The second direction is opposite to the first direction. By way of example, the first direction runs clockwise and the second direction anticlockwise. It has been shown that such a knot is relatively easy to prepare. Thus, the laying or preparation on the main body is relatively simple and the thread required is not very long. In addition, the knot is easy to close or tie, and holds securely.

A preferred embodiment of the invention provides that the thread to form an adaptation knot is laid at least twice around the main body in a first direction and at least once around the functional end in a second direction and that the thread for forming a safety knot is laid at least once around the main body in the second direction. This knot is also easy to prepare and handle with good strength of the tightened knot.

A further preferred embodiment of the invention provides that an element for securing to an object is arranged on the functional end. The element can already be penetrated and/or wound by the thread. By way of example, a synthetic cord for securing to a joint can already be arranged on the thread. Thus, a prepared kit for this application can be offered, which considerably reduces the operational effort.

The method according to the invention for tying a knot with a thread having a functional end and a pull end is characterized by the steps of:

providing a main body, around the outer surface of which the thread in the form of a prepared, still open knot is laid;

bringing an object into contact with the functional end; and pulling on the pull end, so that the thread slides along the outer surface and forms a closed knot.

The same advantages and modifications as described above apply.

A preferred embodiment of the invention provides that the functional end is secured to an attachment point of the main body. This simplifies handling, since only one thread is involved.

A preferred embodiment of the invention provides that the object is penetrated or surrounded by the functional end. In this type of contact with the object, the functional end is laid or run one or more times around the object, to fasten the object or a part or area of the object with the knot. For penetration, the functional end can have a tip or a needle or can be secured to the functional end. Once the object has been penetrated one or more times, the functional end is secured to the main body, whereupon the knot is tightened.

Figure 2:
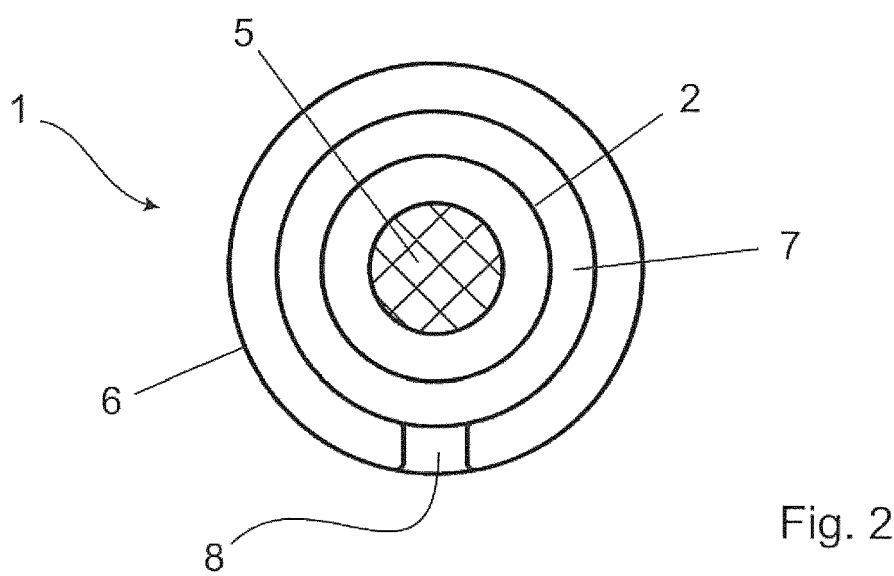
Figure 3:
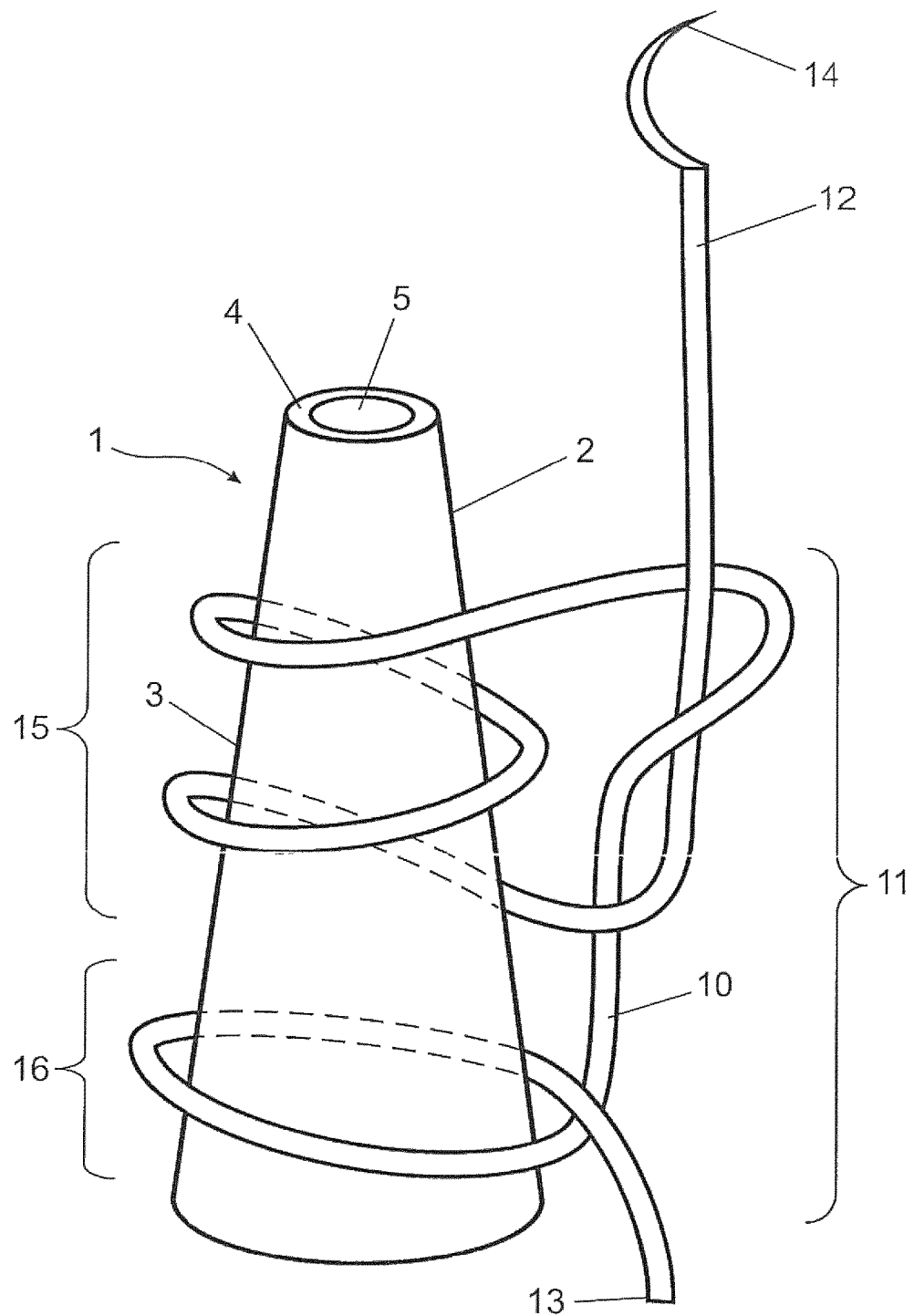
Figure 4:
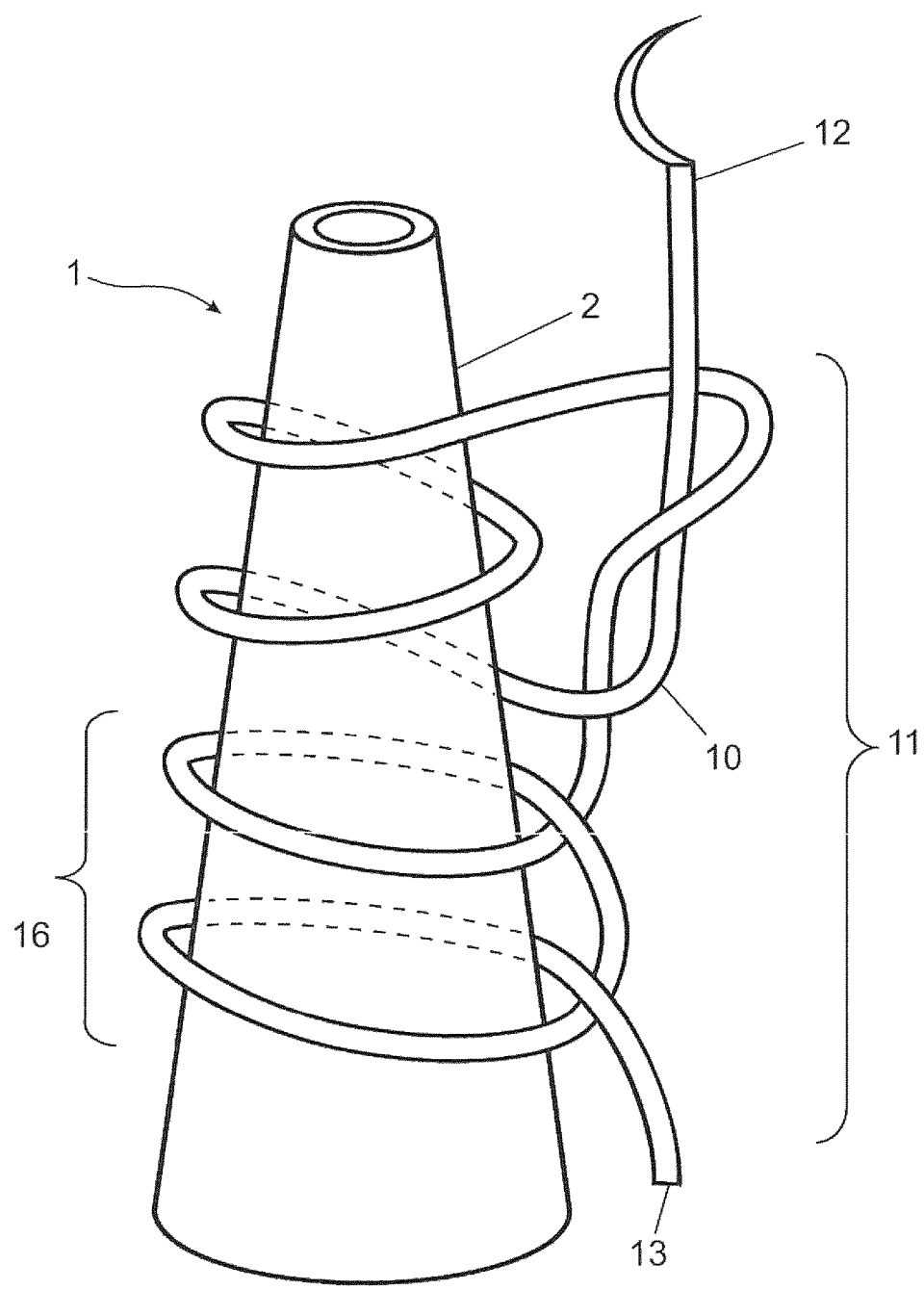
Figure 5:
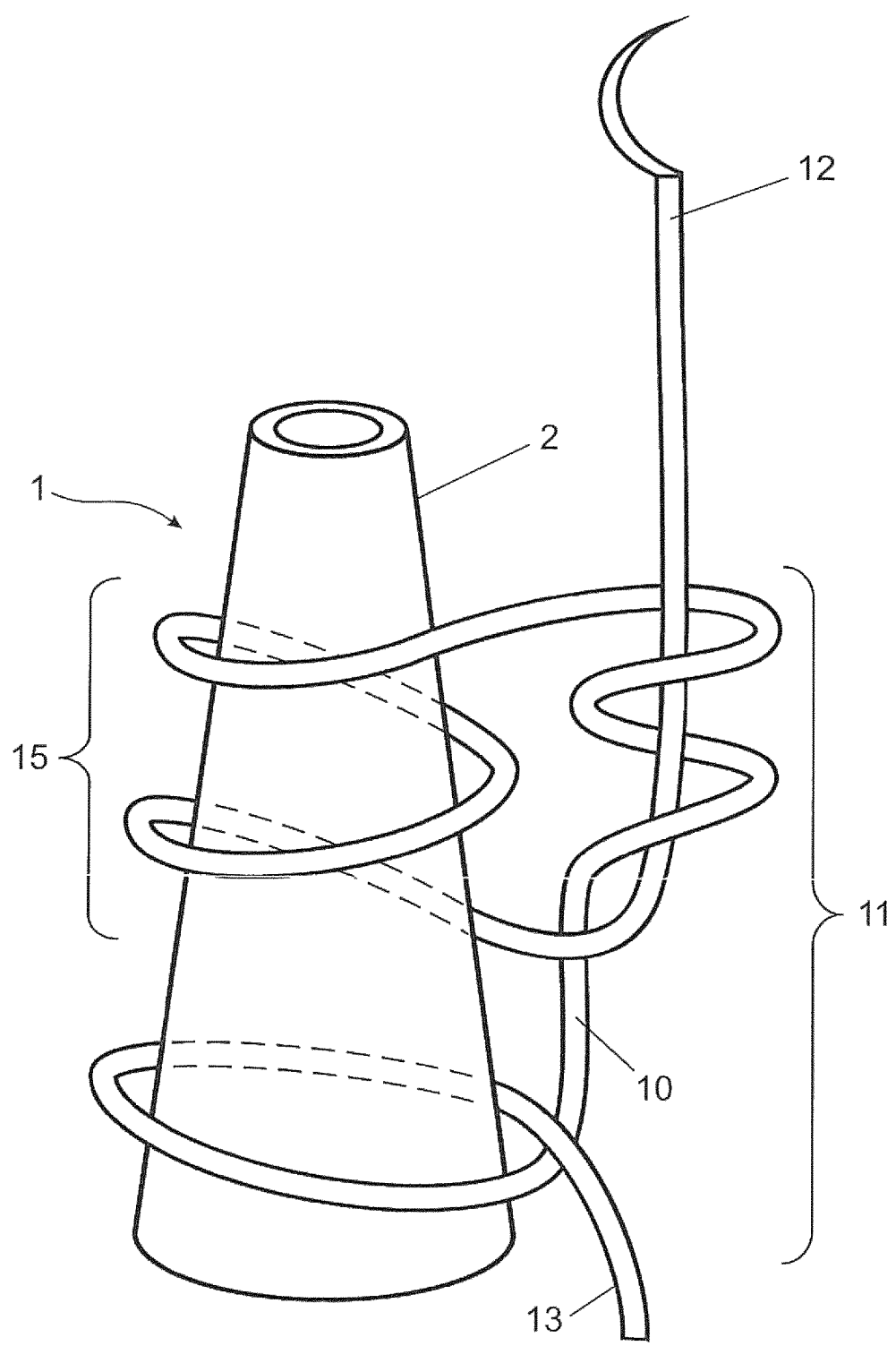
Figure 6:
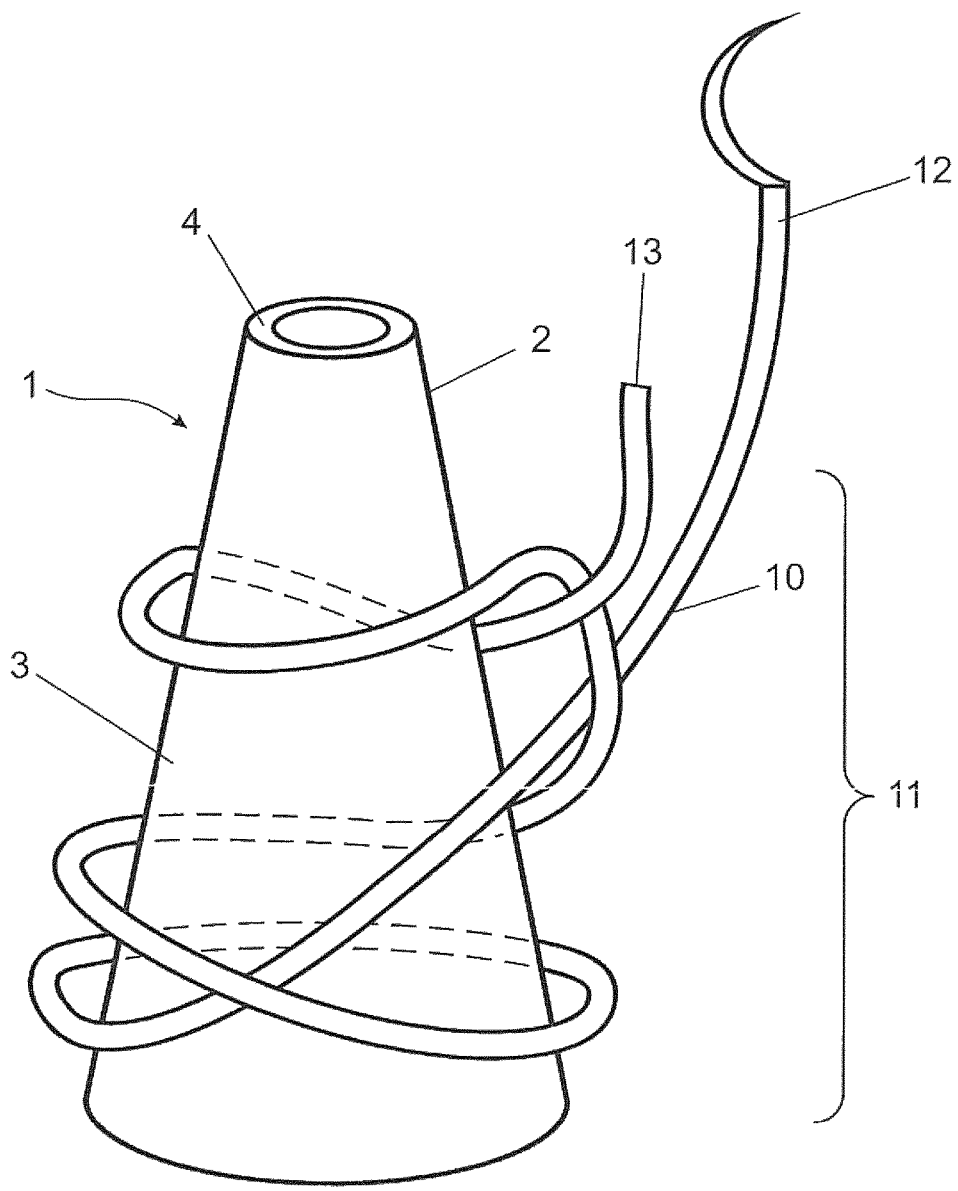
Figure 7:
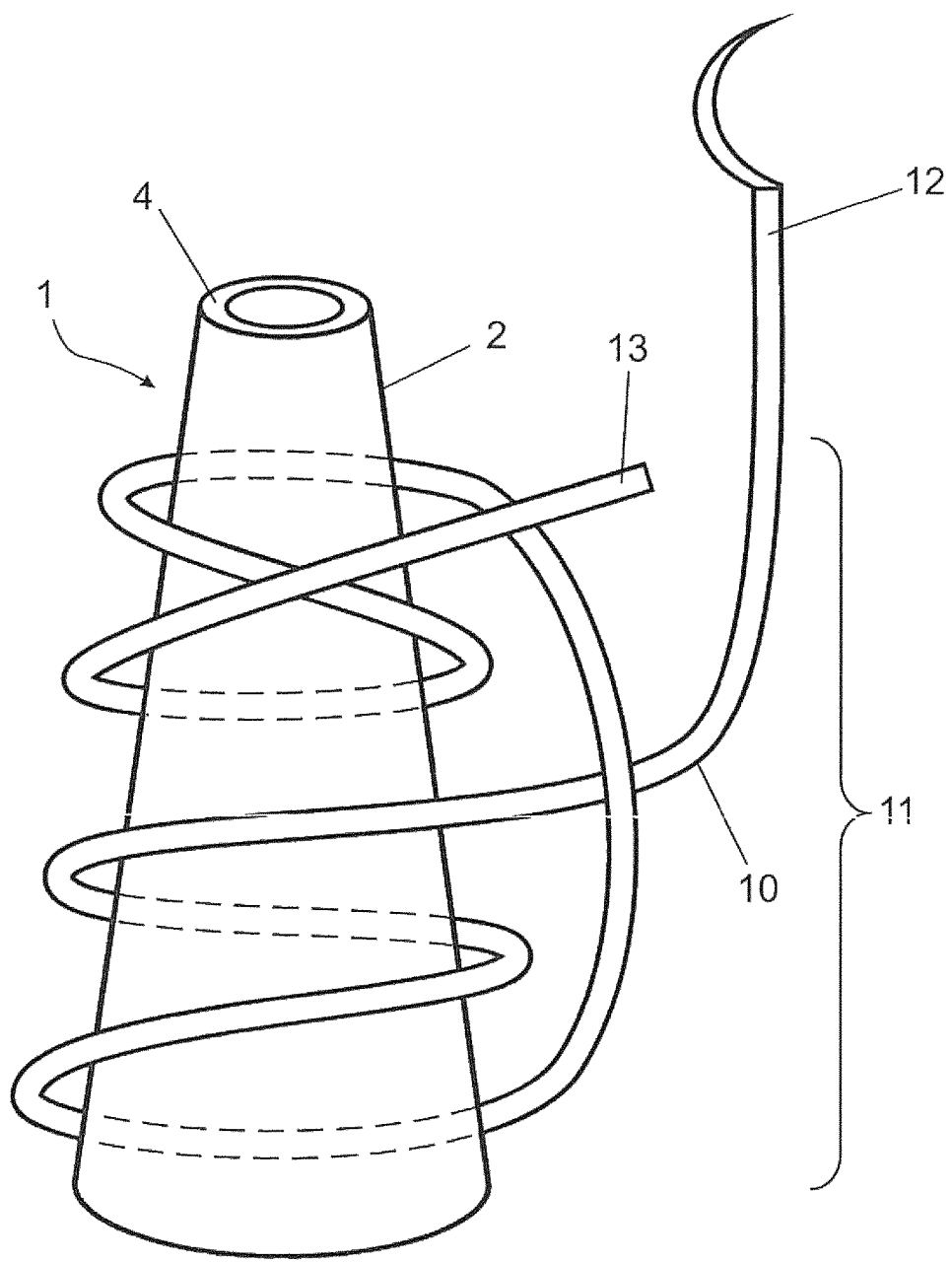
Figure 8:
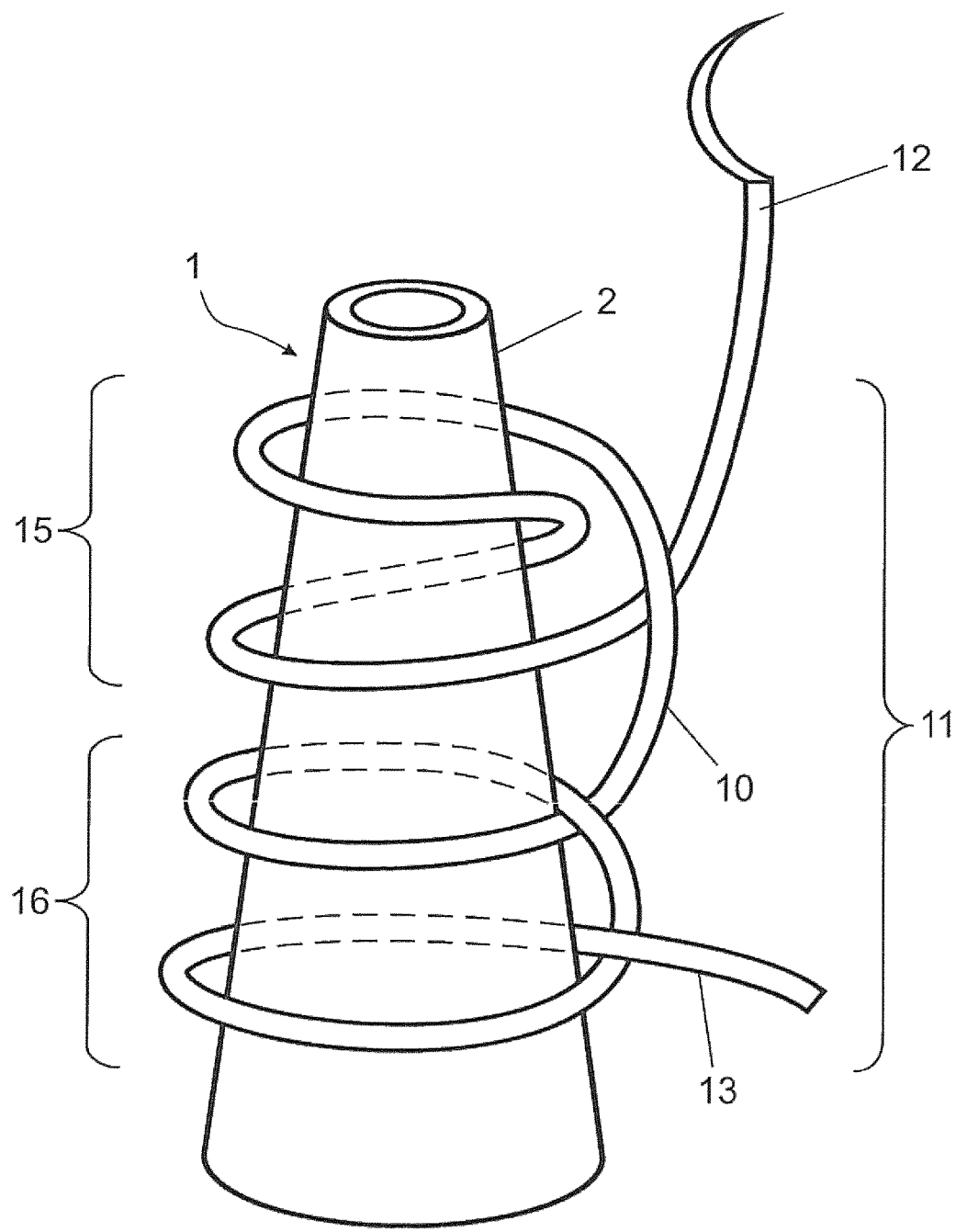
Figure 9:
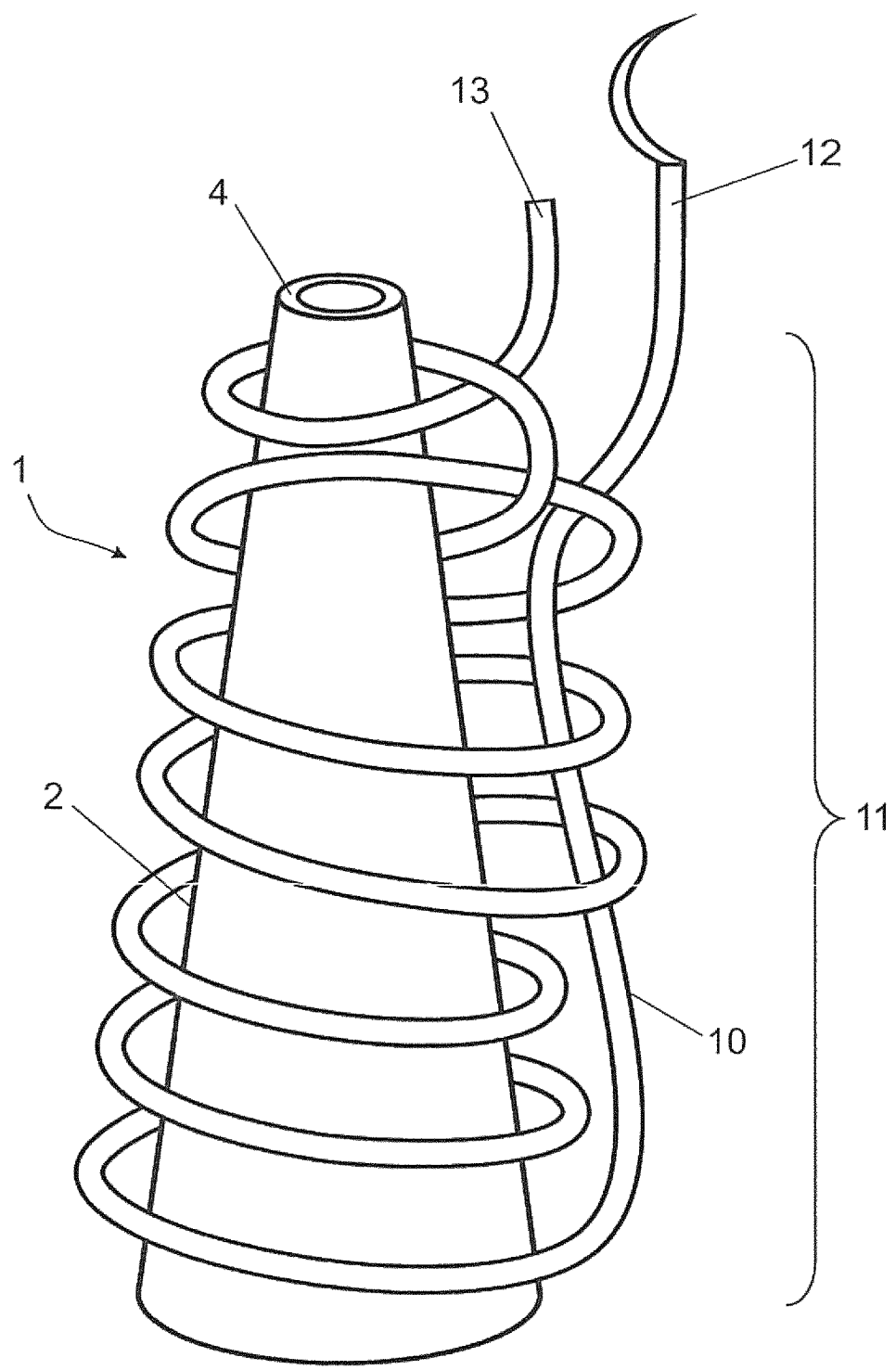
Figure 10:
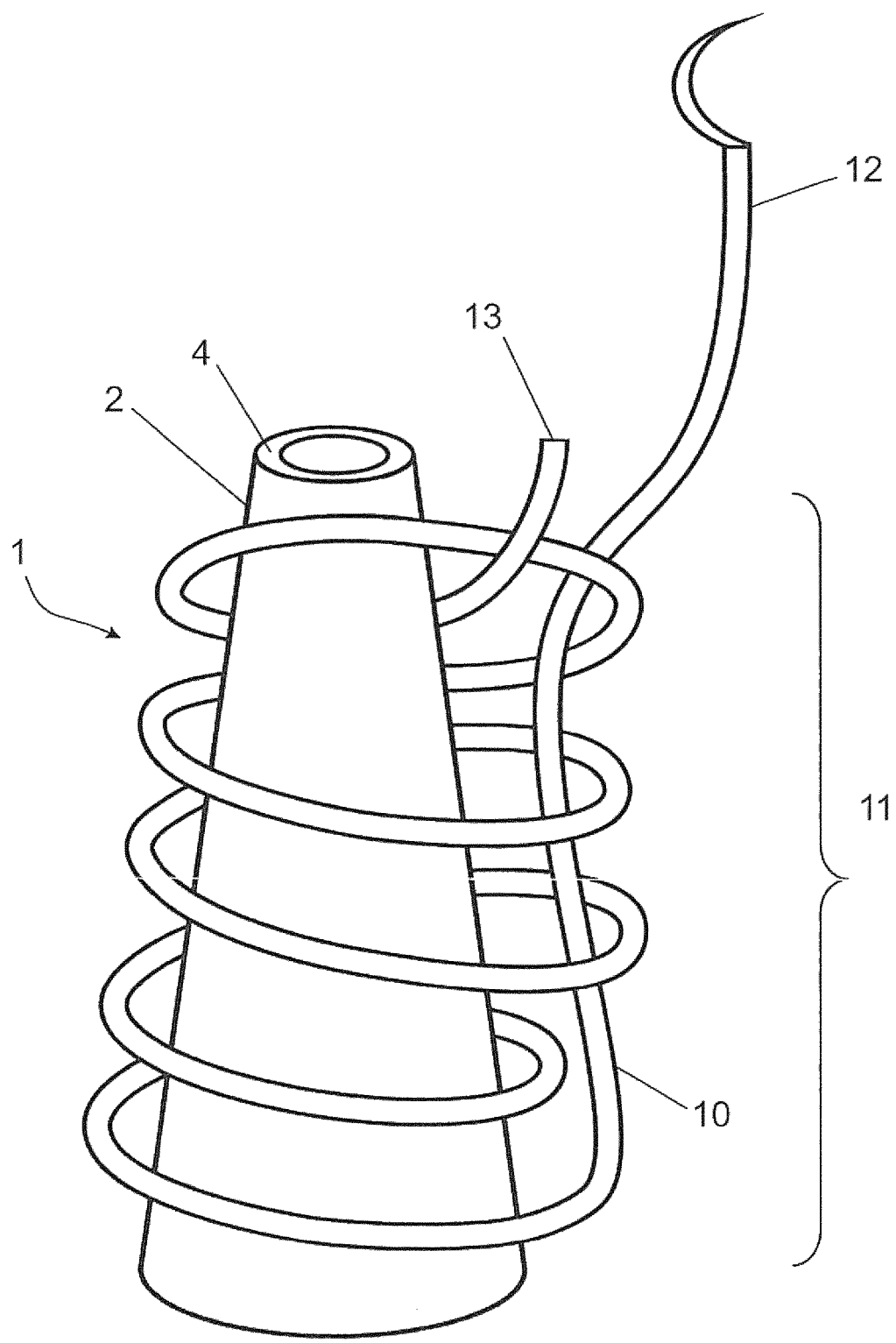
Figure 11:
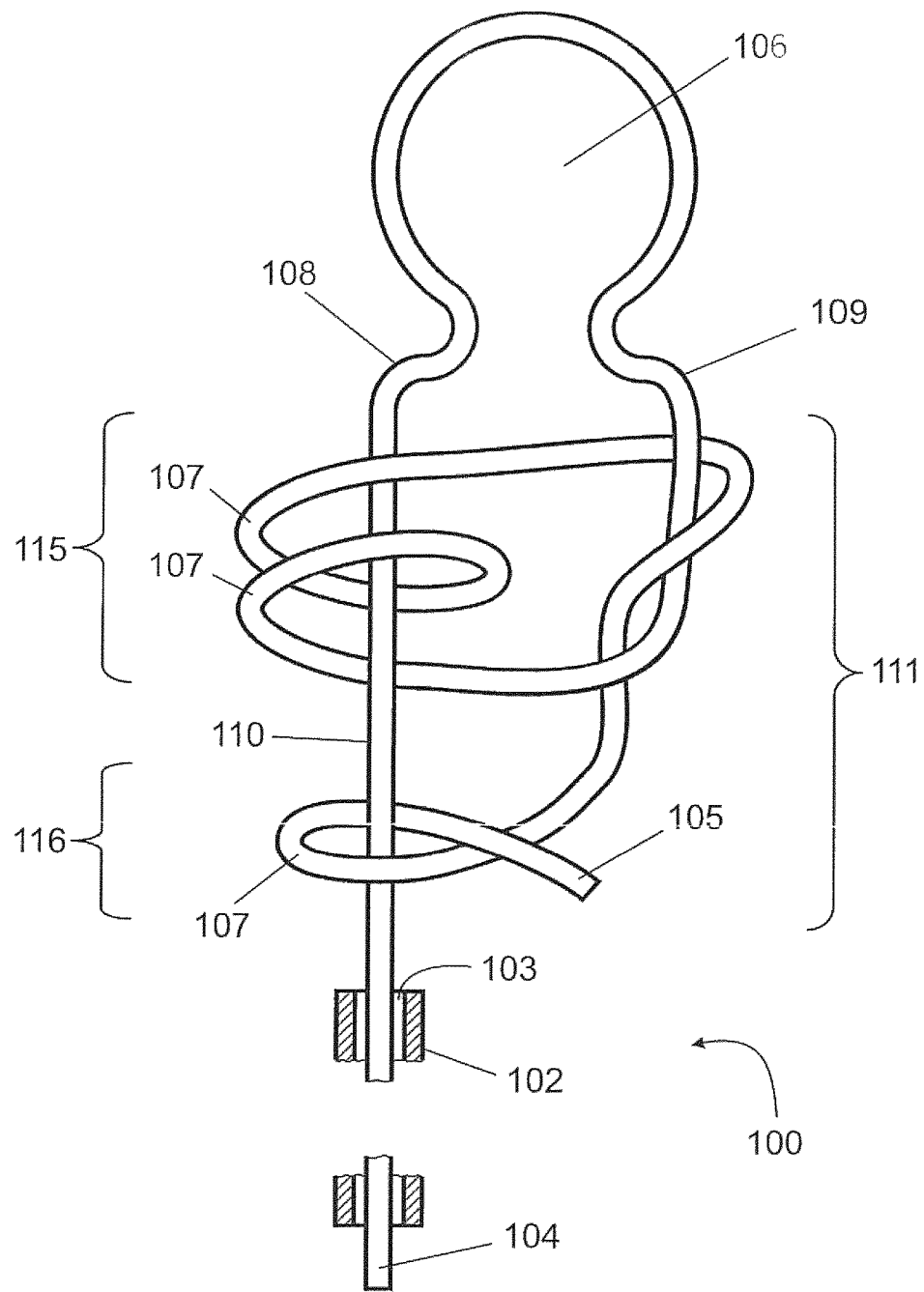
Figure 12:
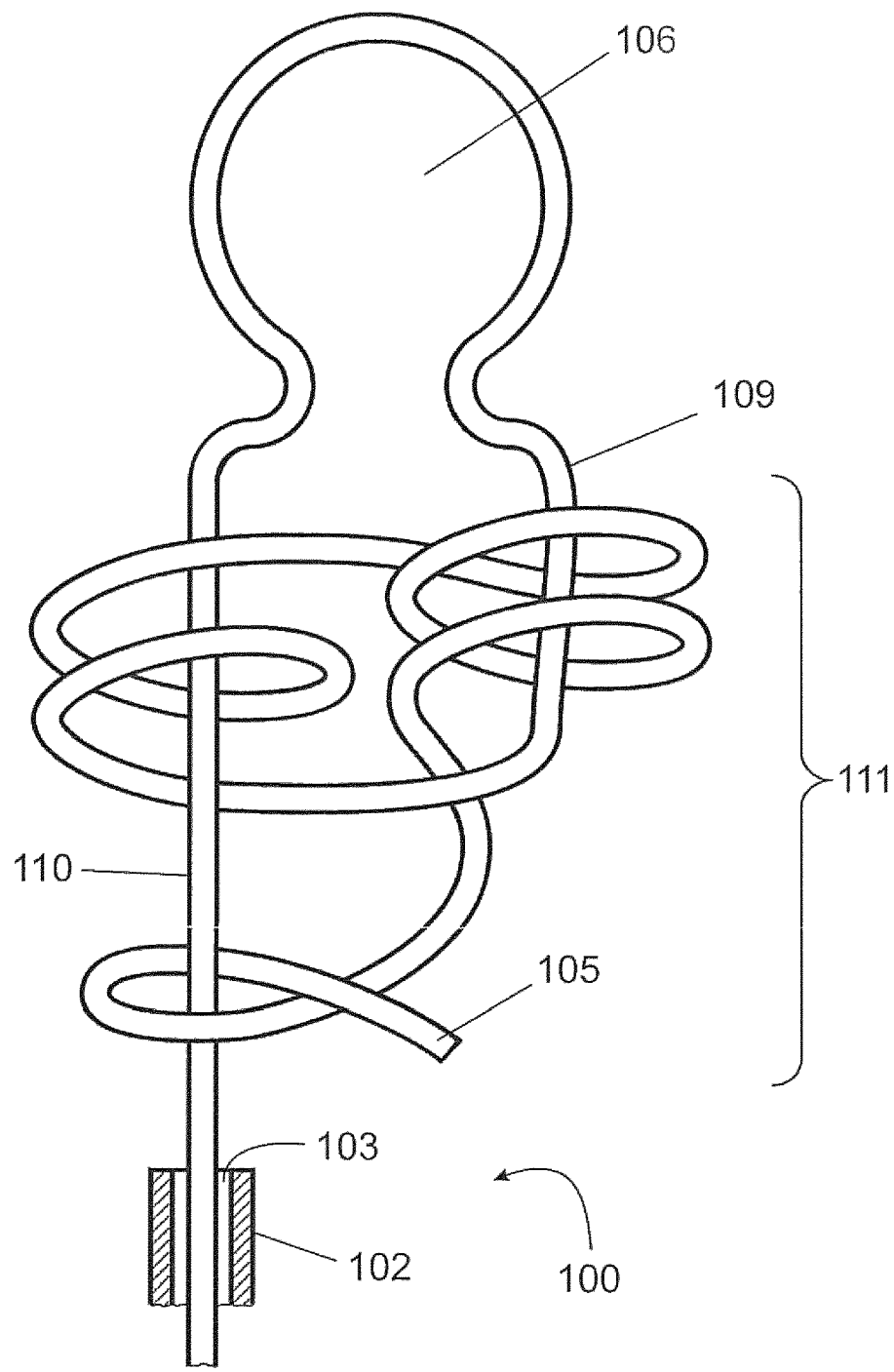

The invention is explained in the following by exemplary embodiments using the associated drawings. These show as follows:

FIG. 1 a perspective view of a device for tying a knot;

FIG. 2 a top view of the device for tying a knot,

FIG. 3 a perspective view of the device with a thread laid for a first knot;

FIG. 4 a perspective view of the device for tying with a thread laid for a further knot;

FIG. 5 a perspective view of the device for tying with a thread laid for a further knot;

FIG. 6 a perspective view of the device for tying with a thread laid for a further knot;

FIG. 7 a perspective view of the device for tying with a thread laid for a further knot;

FIG. 8 a perspective view of the device for tying with a thread laid for a further knot;

FIG. 9 a perspective view of the device for tying with a thread laid for a further knot;

FIG. 10 a perspective view of the device for tying with a thread laid for a further knot;

FIG. 11 a perspective view of a further device for tying a knot;

FIG. 12 the further device for tying a knot with a further knot; and

Figure 13:
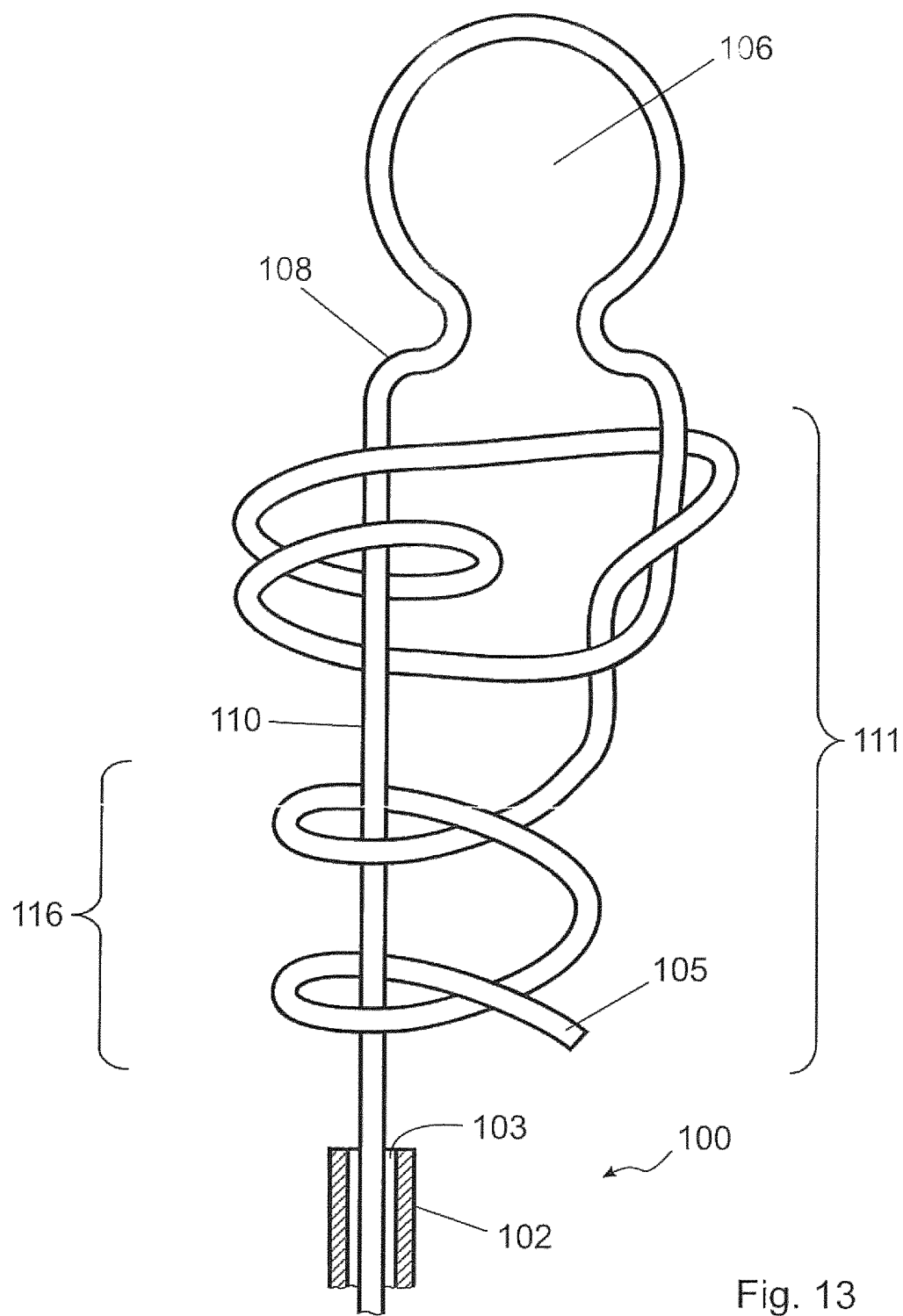

FIG. 13 the further device with a further knot.

FIG. 1 shows a device 1 for tying a knot. For the sake of clarity, the device 1 is initially shown in FIGS. 1 and 2 without thread. In this example, the device 1 comprises a cylindrical main body 2, which is preferably conical. The cylindrical main body 2 has a lateral surface 3 and a top surface 4. A flexible material, such as foam or rubber, or a hook, clip or similar, is provided on or against the top surface 4. The flexible material 5 can be pierced by a thread needle. Instead of the flexible material, another fastening device, such as a hook, a bracket, a clip and/or adhesive can be provided for attaching a thread end. In this way, an attachment point for an end of the thread is defined.

The main body 2 is surrounded by an enveloping body 6. The enveloping body 6 is also cylindrical with an interior 7, that receives the main body 2 and the thread not yet shown here. In the longitudinal direction, i.e. in the direction of the cylinder axis, the main body 2 preferably extends further than the enveloping body 6, so that an upper end of the main body 2 together with the top surface 4 is exposed. This improves visibility and handling when tying the knot.

The enveloping body 6 has an opening 8 running longitudinally, i.e. in the direction of the cylinder axis. The opening 8 can extend over the entire length of the enveloping body 6 or over a section of the length of the enveloping body 6. One or both ends of the thread are later brought out through the opening 8. The enveloping body 6 has a lower area 9, by means of which the enveloping body 6 can be placed upright. It can be provided that the lower area 9 has a full surface configuration, so that the main body 2 stands on an inner surface of the lower area 9. Otherwise the lower area 9 can have a circular configuration, so that the main body 2 is freely movable in the enveloping body 6.

FIG. 2 is a top view of the device 1. As can be seen, the space 7 fully surrounds the main body 2, so that a thread can be laid completely, i.e. through the entire angular range of 360° around the main body 2.

In FIG. 3 the device 1 is shown with a thread 10. The thread 10 is laid in a prepared, still open knot 11 around the lateral surface 3 of the round body 2. A first or functional end 12 of the thread 10 is positioned in the area of the top surface 4 and a second or pull end 13 is located on a base of the main body 2. At the functional end 12 of the thread 10 a needle or tip 14 is arranged, which is able to pierce the flexible material 5 and thus able to be attached in this way.

The thread 10 or the knot 11 has a first area or adaptation knot 15 and a second area or safety knot 16. Here the adaptation knot 15 is turned towards the functional end 12 or the top surface 4. The safety knot 16 is turned towards the pull end 13 or base area of the main body 2. The functional knot 15 meets the requirements placed on the knot 11. By means of the safety knot 16 the finished knot is then secured against coming loose.

For preparation of the knot, the thread 10 is wound in a prepared knot 11 around the cone- or conical-shaped main body. Thus, the thread 10 together with the prepared knot 11 is held securely on the main body until it is actually used. To this end, the thread 10 can rest more closely than shown on the lateral surface 3 of the main body 2. The enveloping body 6 shown in FIGS. 1 and 2 can also secure the thread 10 and the prepared knot 11.

When using the device 1 for tying a knot or when tying a knot, initially an object is looped and/or stitched with the functional end 12 or tip 14. Attaching of the tip 14 and thus the functional end 12 to or in the flexible material 5 or another attaching device then follows. By pulling on the pull end 13 in a direction away from the object, and if necessary moving the device 1, and thus the functional end 12 in the same direction, an inversion of the prepared knot 11 or the thread windings beyond the functional end 12 first takes place and then a tightening of the knot. The arrangement of the thread 10 on the lateral surface 3 guarantees the safe sliding of the thread 10 and automatic securing of the knot. Once the knot has been created, the two thread ends can be cut off with scissors or a similar object.

The device 1 can in particular be advantageously used where multiple consecutive knots are required, where time is of the essence, or where space is limited. Thus, the device 1 can, for example, be used for a ligature or attaching of tissue structures. In this case, the multiple consecutive knotting of the thread has already been prepared with the help of device 1, saving a considerable amount of time. Furthermore, if tissue structures are under tension, then following the tying of a first knot in the conventional sense this knot may loosen, something that is successfully prevented by the device 1. Particularly in Minimally Invasive Surgery (MIC), knotting in the body of the patient represents a major hurdle due to the restricted space, the two-dimensional visuality, and the technical skill required of the surgeon. In this case, the device 1 can be used for stitching or ligature in minimally invasive or even open operations, involving for example intestinal perforations, the peritoneum, vessels, anastomosis, attachments, hemostasis, mesoskeletonization, skin sutures, articulations, foreign body stabilizations, and so on. It is a major advantage that the device 1 can be armed or stocked with monofilament or braided, resorbable or non-resorbable threads of varying strength.

Due to the automatic securing of the ligature by means of the safety knot 16 no additional stabilization knot is required. Thus, the operational complexity is reduced and the operation time shortened. With the device 1, secure knotting can also be performed by non-surgically trained personnel.

The prepared knot 11 in FIG. 3 comprises in the adaptation knot area 15 two loops around the main body 2. In other words, the thread 10 is laid or wound twice in a first direction around the main body 2. With regard to the pull end 13, the thread 10 is wound anticlockwise and with regard to the functional end 12 the thread 10 is wound clockwise. In the adaptation knot area 15, the thread is also wound once around the functional end 12 or a thread area adjacent to the functional end 12. This winding is performed in a second direction opposite to the first direction. To form a safety knot, the thread 10 is laid in the second direction once around the main body 2. This is arranged in the bottom part of the main body 2, e.g. in physical proximity to the pull end 13.

In FIG. 4 the device 1 is shown with a further prepared knot 11. The knot 11 corresponds to the greatest possible extent to the knot 11 from FIG. 3. Here in FIG. 4, to form the safety knot 16, the thread 10 is laid twice around the main body 2 in the second direction.

In FIG. 5 the device 1 is shown with a further prepared knot 11. The knot 11, for its part, corresponds substantially to the knot 11 shown in FIG. 3. In this case, unlike in FIG. 3, with the knot 11 the thread 10 is laid twice in the second direction around the functional end. It is also possible to combine the two knots from FIGS. 4 and 5, so that a knot by way of example comprises one thread laid in the second direction twice around the functional end, and twice around the main body 2 in the second direction to form a safety knot.

In FIG. 6 the device 1 is shown with a further knot 11. With this knot 11, in addition to the functional end 12, the pull end 13 is also located in the area of the cone tip or the top surface 4 of the main body 2. Whereas in the representations of FIGS. 3-5 crossovers or intertwinings of the thread 10 are arranged next to the lateral surface 3 of the main body 2, here in FIG. 6 the crossovers of the thread 10 are arranged in the area of the lateral surface 3. This can potentially improve the handling of the device 1 and the stability of the prepared knot 11.

The knots described in the following are further embodiments of the knots described above. These knots may be advantageous for certain applications. Thus, for example, additional windings can increase the thickness of the knot, so that it is more stable and/or cannot slide through a particular opening. For the tightening of the knot it is generally the case that the pull end 13 is pulled towards the object and that the functional end 12 is pulled away from the object.

FIG. 7 shows the device 1 with a further knot 11. With this knot also, both the functional end 12 and the pull end 13 are located in the area of the top surface 4 of the main body 2.

FIG. 8 shows the device 1 with yet a further knot 11. This knot 11, for its part, has an adaptation knot 15 in an upper area of the main body 2 and a safety knot, double-tied, in a lower area of the main body 2. In the area of the safety knot 16, the pull end 13 of the thread 10 is accessible, while starting from the function knot 15 the functional end 12 is accessible.

FIG. 9 shows the device 1 with a further knot 11. With this knot 11, for its part, both the functional end 12 and the pull end 13 are arranged in the area of the top surface 4 of the main body 2. The thread 10 is laid in a plurality of loops around the main body 2. The main body 2 is wound a total of seven times with the thread 10, wherein the functional end 12 is passed through three of these loops.

FIG. 10 shows the device 1 with a further knot 11. With this knot 11, also, the functional end 12 and the pull end 13 are located in the area of the top surface 4 of the main body 2. Here the thread 10 is looped or wound five times around the main body 2, wherein the functional end 12 is passed through three of the resulting windings.

Using FIGS. 11-13 a further device 100 for tying a knot 111 with a thread 110 is described. The device 100 can be advantageously configured as follows:

1. A device for tying a knot comprising a thread (110) having a functional end (105) and a pull end (104), characterized in that a hollow cylindrical main body (102) is provided, through the cavity (103) of which a part of the thread (110) runs, wherein on one side of the main body (102) the pull end (104) is arranged and wherein on the other side the thread (110) in the form of a prepared, still open knot (111) with a loop (106) is laid, so that by pulling on the pull end (104) away from the loop (106) and on the functional end (105) towards the loop (106) the thread (110) forms a closed knot around an object arrangeable in the loop (106).
2. The device according to Claim 1, characterized in that the diameter of the cavity (103) corresponds to the cross-section of the thread (110).
3. The device according to Claim 1 or 2, characterized in that the thread (110) comprises an adaptation knot (115) turned towards the loop (106) and a safety knot (116) turned towards the main body (102).
4. The device according to any of the preceding claims, characterized in that the thread (110) in a first direction is laid at least twice around a first part (108) of the loop (106), running in the direction of the main body (102), and in that the thread (110) in a second direction is laid at least once around the second part (109) of the loop (106).
5. The device according to any of the preceding claims, characterized in that in order to form an adaptation knot (115) in a first direction, the thread (110) is laid at least twice around a first part (108) of the loop (106), running in the direction of the main body (102), and in that the thread (110) in a second direction is laid at least once around the second part (109) of the loop (106) and in that the thread (110) in order to form a safety knot (116) in the second direction is laid at least once around the first part (108) of the loop (106).

6. A method for tying a knot with a thread (110) comprising a functional end (105) and a pull end (104), characterized by the steps of:

providing a hollow cylindrical main body (102), through the cavity (103) of which a part of the thread (110) runs, wherein on one side of the main body (102) the pull end (104) is arranged and wherein on the other side the thread (110) in the form of a prepared, still open knot (111) with a loop (106) is laid;

arranging an object in the loop (106); and pulling on the pull end (104) and the functional end (105), so that the thread (110) forms a closed knot around the object.

FIG. 11 shows the device 100 for tying a knot 111 from or with a thread 110. The device 100 comprises a hollow cylindrical main body 102, for example in the form of a pipe, with an interior 103. Part of the thread 110 runs through the interior 103. A pull end 104 of the thread 110 protrudes from the main body 102 on a first side. Thus, the pull end 104 is located in a first side of the main body 102. On the opposite other, or second, side of the main body 102 the prepared knot 111 is arranged. A further end or functional end 105 of the thread 110 protrudes from the prepared knot 111. The functional end 105 points in the direction of the main body 102. On the other, opposite, end of the prepared knot 111, e.g. on the end turned away from the main body 102, a loop 106 is provided. The prepared knot 111 is laid or prepared such that the thread 110 forms the open loop 106. The loop can, by way of example, be laid around an object, to which the thread 110 is to be attached or by way of example which is to be constricted or tied up by the thread.

The prepared knot 111 shown in FIG. 11 corresponds to the knot shown in FIG. 3. Here in FIG. 11, the knot 111 is to some extent prepared with a further step beyond the knot 11 from FIG. 3. Unlike FIG. 3, the pull end 104 has already been pulled through the turns or coils 107. In FIG. 3 these coils are arranged on the main body 2, whereas the functional end 12, corresponding to the pull end 104 from FIG. 11, remains free.

Accordingly, the knot 111 for its part, can be subdivided into an adaptation knot and a safety knot 116. To aid understanding, the coil 106 can be broken down into a first part 108, shown on the left here, and a second part 109, shown on the right here. To form the adaptation knot 115 the thread 110 or the two top coils 107 are laid in a first direction twice around the first part 108 of the loop 106. The thread 110 is further laid in a second direction around the second part 109 of the loop 106. To form the safety knot 116 the thread 110 is laid in the second direction once around the first part 108 of the loop 106. The first part 108 of the loop 106 runs to the main body 102, whereas the second part 109 of the loop 106 runs to the functional end 105.

All knots 11 shown in FIGS. 3-10, in connection with the main body 2, can be used accordingly with the device 100. To this end the functional end 12 of FIGS. 3-10 is passed through the loops in each case, lying on the lateral surface 3 of the main body 2. To an extent, therefore, the main body 2 is replaced by the functional end 12, such that the prepared knot 11 of FIGS. 3-10 becomes a prepared knot 111 for the device 100.

FIG. 12 shows the device 100 with a further prepared knot 111. The knot 111 substantially corresponds to the knot 111 shown in FIG. 11. Unlike in FIG. 11, in this case, together with the knot 111, the thread 110 is laid twice in the second direction around the second part 109 of the loop 106. The knot 111 shown in FIG. 12 corresponds to the knot 11 shown in FIG. 5.

FIG. 13 shows the device 100 with a further prepared knot 111. The knot 111 corresponds to the greatest possible extent to the knot 111 from FIG. 11. Here in FIG. 13 116 the thread 110 is laid in the second direction twice around the second part 108 of the loop 106 in order to form the safety knot. The knot 111 shown in FIG. 13 corresponds to the knot shown in FIG. 4.

The device 100 can be used to surround objects with the loop 106 and then to tighten the prepared knot 111, resulting in the object and the thread 110 being joined together. The main body 102 allows the pull end 104 to be pushed or pulled through, to simplify the tightening of the knot. The prepared knot 111 with the loop 106 and the functional end 105 can then be arranged on or behind an object or obstacle. The main body 102 spans or penetrates the object, so that the pull end 104 is located outside the object, and the loop 106 and the functional end 105 are located in, or behind, the object.

In addition to technical applications the device 100 is also suitable for medical purposes. The device 100 can by way of example be used for suturing tissue structures with a self-securing function. The ready-made or prepared knot 111 with the loop 106 can for example be introduced intra-abdominally via a trocar sleeve. The tissue structure intended for ligature is pulled through the loop 106. By simultaneous pulling of the pull end 104 of the loop 106 away from, and pulling of the functional ends 105 towards, the loop 106, the loop 106 or knot 111 is tightened. The described arrangement of the different knots 111 and the hollow cylinder 102 guarantees the safe sliding and automatic stabilization of the ligature. Following tightening of the loop 106 or formation of the knot 111, the functional end 105 of the thread 110 is cut intra-abdominally in the vicinity of the ligature with scissors.

Due to the automatic securing of the ligature no additional stabilization knot is required. Thus, the complexity is reduced and the operation time shortened. Particularly in structures under tension, the available looping systems or an extracorporeal knot may lead to the knot loosening. The device according to the invention 100 removes these disadvantages.

The device 100 can be applied in the ligature of, for example the Appendix vermiformis (appendix), on the Ductus cysticus (cystic duct), in vessels, retrieval of tissue samples etc., during laparoscopic operations or in open surgery under difficult and unclear conditions of the operation site. The arming of the apparatus with monofilament or braided and resorbable/non-resorbable threads of varying strength is a big advantage.

The invention claimed is:

1. A device for tying a knot, comprising a thread (10) with a functional end (12) and a pull end (13), wherein a main body (2) is provided, around the outer surface (3) of which the thread (10) is laid in the form of a prepared, still open knot (11), such that as a result of pulling on the pull end (13), the thread slides along the outer surface (3) and forms a closed knot, characterized in that the thread (10) comprises an adaptation knot (15) turned towards the functional end (12) and a safety knot (16) turned towards the pull end (13).

2. The device according to claim 1, characterized in that the functional end (12) is attachable to an attachment point of the main body (2).

3. The device according to claim 2, characterized in that the attachment point is arranged on a top surface (4) of the main body (2), on an inside of the main body (2) or on the outer surface (3).

4. The device according to claim 1, characterized in that fastening means for connecting to an object and/or functional means for functionally connecting to an object are arranged on the thread (10) before the functional end (12).

5. The device according to claim 4, characterized in that the fastening means and/or the functional means comprise a needle.

6. The device according to claim 2, characterized in that flexible material is arranged at the attachment point and in that a tip (14), which is able to pierce the flexible material (5), is arranged on the functional end (12).

7. The device according to claim 2, characterized in that the attachment point and the functional end (12) are connectable by means of a bonded connection, wherein the connection can be nondetachable or re-closable.

8. The device according to claim 1, characterized in that an enveloping body (6) at least partly surrounding the main body (2) and thread (10) is provided, wherein the enveloping body (6) comprises at least one opening (8) arranged in the area of the lateral surface (3) for the functional end (12) and/or the pull end (13).

9. The device according to claim 1, characterized in that the main body (2) has a configuration that is cylindrical or conical.

10. The device according to claim 1, characterized in that the thread (10) is laid in a first direction at least twice around the main body (2) and in a second direction at least once around the functional end (12).

11. The device according to claim 1, characterized in that, in order to form an adaptation knot (15), the thread (10) is laid at least twice around the main body (2) in a first direction and at least once around the functional end (12) in a second direction and in that the thread (10) in order to form a safety knot (16) in the second direction is laid at least once around the main body (2).

* * * * *